(12) United States Patent
Krueger et al.

(10) Patent No.: US 8,822,738 B1
(45) Date of Patent: Sep. 2, 2014

(54) PROCESS FOR THE PREPARATION OF HYDROXYTYROSOL

(71) Applicant: Wacker Chemie AG, Munich (DE)

(72) Inventors: Benno Krueger, Burgkirchen (DE); Gerald Fleischmann, Burghausen (DE); Hermann Petersen, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/188,837

(22) Filed: Feb. 25, 2014

(30) Foreign Application Priority Data

Mar. 5, 2013 (DE) .......................... 10 2013 203 753

(51) Int. Cl.
*C07C 37/055* (2006.01)
*C07C 37/50* (2006.01)
*C07C 37/01* (2006.01)

(52) U.S. Cl.
CPC ................................... *C07C 37/055* (2013.01)
USPC .......................................... 568/772; 568/763

(58) Field of Classification Search
None
See application file for complete search history.

(56) References Cited

U.S. PATENT DOCUMENTS 8,017,815 B2 * 9/2011 Breuninger et al. .......... 568/764

FOREIGN PATENT DOCUMENTS

| CN | 101891595 A | 11/2010 |
|---|---|---|
| CN | 102344344 A | 2/2012 |
| KR | 1020070038702 A | 4/2007 |
| WO | 2007009590 A1 | 1/2007 |
| WO | 2008107109 A1 | 9/2008 |
| WO | 2008110908 A1 | 9/2008 |
| WO | 2009153374 A1 | 12/2009 |
| WO | 2012003625 A1 | 1/2012 |
| WO | 2012006783 A1 | 1/2012 |

OTHER PUBLICATIONS

G. Schill et al., Reductive Cleavage of 2,2-Dialkyl-1,3-benzodioxole Derivatives with Diisobutylaluminium Hydride_Synthesis of a [2]-Catenane having a 22-Membered Macroheterocycle, Chem. Ber., 1980, pp. 3697-3705, 113.
A. Gambacorta et al., High-yielding Synthesis of Methyl Orthoformate-protected Hydroxytyrosol and its Use in Preparation of Hydroxytyrosyl Acetate, Molecules 2007, pp. 1762-1770, 12.

* cited by examiner

*Primary Examiner* — Brian J Davis
(74) *Attorney, Agent, or Firm* — Caesar, Rivise, Bernstein, Cohen & Pokotilow, Ltd.

(57) ABSTRACT

A process for preparing hydroxytyrosol, wherein a compound

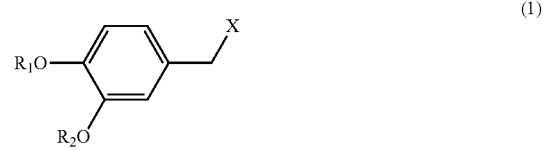

(1)

where X is $CH_2OH$ or $CH_2OM$ (M=Li, Na, K, Mg, Ca), $R_1$ and $R_2$ are identical or different and are C1-C8 alkyl radical, benzyl radical, alkyl- or halogen-substituted benzyl radical or arylalkyl radical, where $R_1$ and $R_2$ can also be linked via

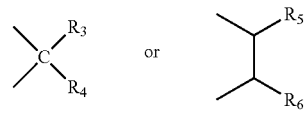

to give a ring, $R_3$, $R_4$, $R_5$ and $R_6$ are identical or different and are hydrogen or C1-C6 alkyl radical, aryl radical, alkyl-substituted aryl radical, where $R_5$ and $R_6$ can also be linked via $-(CH_2)_4-$, $-(CH_2)_5-$ or $-(CH_2)_6-$ to give a ring, is reacted with an aluminum compound $AlR_7R_8R_9$ (2), where $R_7$, $R_8$ and $R_9$ are identical or different and are H or C1-C8 alkyl radical, and then an aqueous solution of a hydroxycarboxylic acid is added to form a clear homogeneous acidic solution with a pH<3, and hydroxytyrosol is extracted therefrom.

18 Claims, No Drawings

PROCESS FOR THE PREPARATION OF HYDROXYTYROSOL

BACKGROUND

The invention relates to a process for the preparation of hydroxytyrosol (3,4-dihydroxyphenylethanol).

Hydroxytyrosol is an effective antioxidant and has aroused great interest in recent years on account of its positive effects for health. Hydroxytyrosol is an active component of the Mediterranean diet. The European Food Safety Authority (EFSA) has verified polyphenols from olives as having a positive Health Claim, with a daily hydroxytyrosol dose of at least 5 mg being recommended. An antiinflammatory effect of hydroxytyrosol has also been described. Moreover, there are studies which show that hydroxytyrosol in vitro has antimicrobial properties against pathogens of the respiratory tract and of the gastrointestinal tract, such as against some strains of the genus *Vibrio, Salmonella* or *Staphylococcus* and that the dosage used can definitely compete with those of antibiotics, e.g. ampicillin. Moreover, the substance is attributed a neuroprotective and an anti-proliferative and pro-apoptotic effect. These properties make hydroxytyrosol a very interesting and much researched substance which is used in pharmaceuticals, food supplements, functional foods and also in cosmetics.

Hydroxytyrosol which has hitherto been available in the market originates for the large part from olives, olive leaves or wastewater which is produced during the production of olive oil and is supplied in the form of an extract. The proportion of hydroxytyrosol in these products is very small in most cases. Examples thereof are HIDROX™ with a hydroxytyrosol content below 12%, or OPEXTAN™ which contains about 4.5% hydroxytyrosol.

Besides the isolation of natural hydroxytyrosol from olives, numerous processes are described for preparing this substance synthetically. For example, WO 2008/107109 describes a process for the preparation, by reduction, of 4-(chloroacetyl)-1,2-dihydroxybenzene (4-(chloroacetyl) catechol) with the help of catalysts such as palladium/carbon. However, the preparation of the starting compound 4-(chloroacetyl)catechol requires high temperatures and long reaction times.

WO 2007/009590 A1 describes a process for the preparation of hydroxytyrosol via 3,4-dihydroxymandelic acid, which is hydrogenated by metal catalysts such as palladium/carbon to give 3,4-dihydroxyphenylacetic acid. Subsequently, the reduction to hydroxytyrosol takes place. According to the examples, the hydroxytyrosol obtained has purities between 67.9% and 93.8%. Apart from one example, which describes a product with a purity of 98% without stating the pure yield by recrystallization, the precursor obtained from 3,4-dihydroxymandelic acid ester, methyl 3,4-dihydroxyphenyl acetate, is described as product with purities between 51.2% and 83.5%.

The abstract for KR 2007 038702 A describes a synthesis via styrene oxide derivatives. The starting substance is hydrogenated in the presence of a precious metal catalyst such as palladium on activated carbon. Epoxides are unacceptable as regards a mutagenic or carcinogenic effect, meaning that traces in the end product are problematic for use in the food sector.

In the specified hydrogenation reaction, esters or acid analogs of hydroxytyrosol are reduced. Disadvantageously, precious metal catalysts or toxic catalysts such as nickel are required for this purpose.

WO 2008/110908 A1 describes a process starting from tyrosol. In the process, firstly the hydroxyethyl group is protected by means of different reagents, and then a second hydroxy group is inserted into the aromatic ring in the hydroxyethyl-protected tyrosol derivatives using derivatives of iodobenzoic acid. Both the starting material tyrosol and the oxidizing agents are very expensive compounds. The reaction is complex on account of the many feed materials. There are no details relating to the purity of the hydroxytyrosols obtained by the different processes.

WO 2009/153374 describes a preparation process starting from safrole. Both safrole and the HMPT used in the reaction are carcinogenic, meaning that this process is unsuitable for producing food supplements on account of the possible impurities.

WO 2012/003625 describes the preparation of hydroxytyrosol by ozonolysis of eugenol at low temperature and subsequent reduction of the resulting product. The demethylation then takes place with the help of a Lewis acid and a mercaptan. The low-temperature ozonolysis is an expensive reaction step in which secondary reactions such as oxidation of the phenolic group cannot be excluded. The demethylation with the help of extremely foul-smelling substances such as mercaptans, which moreover is not easy, makes the preparation of products for use as food supplements difficult. Both reaction steps evidently produce contaminated products, which are described as red oil.

WO 2012/006783 A1 describes the preparation of hydroxytyrosol starting from low cost pyrocatechol which, following protection of the phenolic groups, is halogenated. The halogenated protected pyrocatechol is then reacted with magnesium to give the corresponding Grignard compound, which is reacted with ethylene oxide in order to introduce the hydroxyethyl group into the aromatic ring. The demethylation takes place in turn with the help of ethanethiol (ethyl mercaptan) aluminum chloride or hydrogenolysis of benzyl ethers with the help of Pd/C and $H_2$.

For all three described processes there is considerable purification complexity for each of the three stages. Moreover, the ethoxylation takes place with a considerable excess of ethylene oxide; a formation of oligomeric glycol units is therefore probable. Depending on the protective group, the demethylation takes place by Lewis acid and ethylmercaptan, with the problems already described, or by hydrogenolysis. The yields of hydroxytyrosol are 32% to 70% in the three described processes. The products obtained are yellow to red oils, which suggests considerable impurities. Possible impurities due to traces of carcinogenic ethylene oxide are problematic for use in the food supplement sector.

The abstract for CN102344344 describes a process in which 3,4-dialkoxyphenylacetic acid alkyl ester (alkyl C1-C5 and benzyl) are reduced and demethylated in one step with the help of sodium in alcohols. The advantage of the process is the one-pot reaction, although it is known that the cleavage of aryl ethers with the help of sodium in alcohols is associated with considerable byproduct formation since a cleavage of the aryl ether between oxygen and aromatic ring also arises. In the examples, the yield is at most 50%. In all of the examples, purification by column chromatography is required.

The abstract for CN101891595 describes a very complex four-stage process for the preparation of hydroxytyrosol with unknown purification complexity and impurities.

The reductive cleavage of 2,2-dialkyl-1,3-benzodioxole derivatives with the help of diisobutylaluminum hydride is described by G. Schill et al.; Chem. Ber. 113, 3697-3705, 1980. For the cleavage of the catechol acetals, a more than 13-fold amount of diisobutylaluminum hydride is used in the molar ratio.

A. Gambacorta, D. Tofani, A. Migliorini; Molecules 2007, 12, 1762-1770 describe a three-stage hydroxytyrosol synthesis which starts from methyl 3,4-dihydroxyphenylacetate. The process is complex and methyl 3,4-dihydroxyphenylacetate is not a standard commercial substance and, according to this literature reference, has to itself be prepared in a multistage process.

DESCRIPTION OF THE INVENTION

It was an object of the present invention to provide an effective and low cost process which makes it possible to prepare hydroxytyrosol easily and in high purity.

This object is achieved by a process in which a compound of the general formula (1)

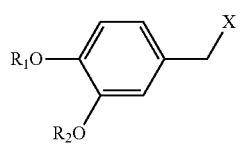

(1)

where X is $CH_2OH$ or $CH_2OM$ (M=Li, Na, K, Mg, Ca), $R_1$ and $R_2$ are identical or different and are alkyl radical having 1 to 8 carbon atoms, benzyl radical, alkyl- or halogen-substituted benzyl radical or arylalkyl radical, where $R_1$ and $R_2$ can also be linked via

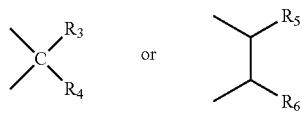

to give a ring,
$R_2$, $R_4$, $R_5$ and $R_6$ are identical or different and are hydrogen or alkyl radical having 1 to 6 carbon atoms, aryl radical, alkyl-substituted aryl radical,
where $R_5$ and $R_6$ can also be linked via $—(CH_2)_4—$, $—(CH_2)_6—$ or $—(CH_2)_6—$ to give a ring,
is reacted with an aluminum compound of the formula (2)

$$AlR_7R_8R_9 \quad (2)$$

where $R_7$, $R_8$ and $R_9$ are identical or different and are H or alkyl radical having 1 to 8 carbon atoms, and then
an aqueous solution of a hydroxycarboxylic acid is added in an amount such that a clear homogeneous acidic solution with a pH<3 is formed,
hydroxytyrosol is extracted from this aqueous clear homogeneous acidic solution with the help of an organic solvent and the organic solvent is removed.

In the process according to the invention, reducing conditions prevail during the entire reaction. Consequently, an oxidation of the sensitive hydroxytyrosol cannot arise. Furthermore, under these conditions no secondary reactions take place, such as elimination of water from the 2-phenylethanol group. The hydroxytyrosol obtained from this process is a colorless clear liquid.

Preferably, X is $CH_2OH$.

Preferably, $R_1$, $R_2$ are identical or different and are alkyl radical having 1 or 2 carbon atoms.

The alkyl-substituted benzyl radical is preferably a benzyl radical substituted with a methyl radical in position 2, 3 or 4.

The arylalkyl radical is for example a phenylethyl radical, phenylpropyl radical, tolylethyl radical.

Preferably, $R_3$, $R_4$, $R_5$ and $R_6$ are identical or different and are hydrogen or alkyl radical having 1 or 2 carbon atoms.

The alkyl-substituted aryl radical is preferably substituted with a methyl radical in position 2, 3 or 4.

The arylalkyl radical is, for example, a phenylethyl radical, phenylpropyl radical, tolylethyl radical.

The compound of the formula (1) is preferably a compound selected from the group 2-(3,4-dialkoxy)phenylethanol, 2-(3,4-methylenedioxyphenyl)ethanol, 2-(2,2-dialkylbenzo[1,3]-dioxol-5-yl)ethanol, 2,3-dihydro-1,4-benzodioxin-6-yl)ethanol, and the salts of the aforementioned alcohols.

It is particularly preferably 2-(3,4-dimethoxy)phenylethanol or 2-(3,4-methylenedioxyphenyl)ethanol.

The compound of the formula (2) is preferably diisobutylaluminum hydride or triisobutylaluminum.

The reaction preferably takes place at a temperature between 0° and 200° C., based on a pressure of 1013 hPa, particularly preferably between 20° and 170° C., based on a pressure of 1013 hPa.

The reaction preferably takes place over a period of 1 to 25 hours, particularly preferably over a period of 5 to 20 hours.

Preferably, the compounds of the formula (1) and the compounds of the formula (2) are used in a molar ratio of compound of formula (1):compound of formula (2) of 1:3 to 1:6. Preferably 1:3 to 1:4. If the compound of the formula (1) is used in deficit, i.e. less than 1:3 mol of the compound 1, based on 1 mol of compound 2, then the reaction products formed are only the two monoethers of hydroxytyrosol (2-(3-hydroxy-4-alkoxy)phenylethanol and 2-(4-hydroxy-3-alkoxy)phenylethanol, and the unreacted diether (2-(3,4-dialkoxy)phenylethanol). When reacting (2-(3,4-dimethoxy)phenylethanol), the byproducts formed are only 2-(3-hydroxy-4-methoxy)phenylethanol and 2-(4-hydroxy-3-methoxy)phenylethanol. These compounds are also present in natural olive extracts or natural olive oil and occur as metabolites of hydroxytyrosol.

The reaction of the compound of the formula (1) with an aluminum compound of the formula (2) preferably takes place in an organic solvent. Suitable solvents for the reaction are aliphatic or aromatic hydrocarbons, which may be linear, branched or cyclic. It is preferably an aromatic hydrocarbon. Particular preference is given to toluene, xylene (all isomers), ethylbenzene, diethylbenzene (all isomers), 1,3,5-trimethylbenzene, propylbenzene, isopropylbenzene (cumene), butylbenzene or cyclic alkylbenzenes such as indane, $C_1$ or $C_2$ alkylnaphthalenes or partially hydrogenated naphthalenes such as e.g. tetralin.

Part of the process according to the invention is a simple work-up process of the resulting reaction mixture which makes do without complex purification steps and leads directly to pure hydroxytyrosol. Surprisingly, it has been found that upon work-up of the resulting reaction mixture with the help of an aqueous solution of a hydroxycarboxylic acid, the hydroxytyrosol can then be extracted from the aqueous acid phase virtually quantitatively in the usual manner with the help of an organic extractant.

Firstly, when the reaction is complete, the reaction mixture is preferably admixed with an aqueous solution of a hydroxycarboxylic acid.

The aqueous solution of a hydrocarboxylic acid is preferably an aqueous solution of citric acid, malic acid, lactic acid, glycolic acid or tartaric acid.

Preferably, the aqueous solution comprises hydroxycarboxylic acid in a concentration of 5 to 50% (v/v).

What happens here is that the hydroxytyrosol transfers from the organic phase to the aqueous phase, with hydrophobic impurities remaining in the organic phase.

The hydroxytyrosol is then extracted from the aqueous phase using an organic solvent. As a result, the aluminum salts are separated off from the hydroxytyrosol.

The extractant is preferably ethers, carboxylic acid esters, carboxylic acid amides, acetals, ketals, alcohols or alkylamines. Preference is given to ethers or carboxylic acid esters.

Of particular suitability here are compounds which form an azeotrope with water which has a boiling point of <100° C., meaning that the water present in the organic phase is removed upon distilling off the solvent.

Particular preference is given to using carboxylic acid esters such as ethyl acetate, methyl acetate, isopropyl acetate, particularly preferably ethyl acetate.

After removing the extractant, e.g. by distillation, hydroxytyrosol is obtained in high yields, which are understood to mean preferably yields >80%, particularly preferably yields >90%, and in high purity.

Compounds of the formula (1) are commercially available or can be prepared by customary reduction processes from standard commercial raw materials such as 2-(3,4-methylenedioxyphenyl)acetic acid, 2-(3,4-dimethoxyphenyl)acetic acid, and alkyl esters thereof (alkyl C1-C4 also branched), and benzyl esters.

The compounds of the formula (1) can also be generated in situ and be further reacted immediately to give hydroxytyrosol. In this case, in the process according to the invention, instead of compounds of the formula (1), those of the formula (3) are used,

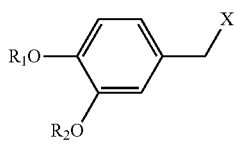

(3)

where X is $COOR_{10}$,
$R_1$ and $R_2$ have the meaning given for compounds of the formula (1) and $R_{10}$ is H, $C_1$ to $C_4$ alkyl radical, benzyl radical, preferably H, methyl radical, ethyl radical.

The compounds of the formula (3) are preferably 2-(3,4-dialkoxy)phenylacetic acid, 2-(3,4-methylenedioxyphenyl)acetic acid, 2-(2-alkylbenzo[1.3]-dioxol-5-yl)acetic acid, 2,3-dihydro-1,4-benzodioxin-6-yl)acetic acid, and $C_1$ to $C_4$ alkyl or benzyl esters of the aforementioned acids.

It is particularly preferably 2-(3,4-dialkoxy)phenylacetic acid or their methyl or ethyl esters, and 2-(3,4-methylenedioxyphenyl)acetic acid or their methyl or ethyl esters.

Reduction and dealkylation take place here either in one step with compounds of formula (2), where at least one of the radicals ($R_7$, $R_8$ or $R_9$) is H, such as e.g. diisobutylaluminum hydride, or with two different reagents sequentially in a one-pot process. In the second-mentioned case, the reduction step takes place initially with reducing agents such as e.g. lithium aluminum hydride, sodium borohydride, diisobutylaluminum hydride, alkoxyaluminates such as sodium bis(2-methoxyethoxy)aluminum dihydride to give the compounds of the formula (1), and dealkylation takes place as described for compounds of the formula (1) with a compound of the formula (2).

Reduction and dealkylation can take place in the same solvent, although the reduction can also take place in a different solvent to the dealkylation, with solvent exchange being possible without isolation of the substance of the formula (1) or salts thereof obtained as an intermediate. In the first-mentioned case, the solvents already mentioned for the process according to the invention are preferably used; in the second-mentioned case solvents such as ethers, e.g. diethyl ether, diisopropyl ether, dibutyl ether, 1,2-dimethoxyethane, also cyclic such as e.g. tetrahydrofuran, methyltetrahydrofuran, are used. Further work-up takes place as already described.

The process according to the invention produces a high yield of isolated hydroxytyrosol with a small number of synthesis steps. In this connection, high yield is preferably to be understood as meaning a yield of >80%, preferably >90%.

All of the materials preferably used in the process are commercially available at any time at low cost; of particular advantage is the use of the commercially inexpensively available starting materials, 2-(3,4-dimethoxyphenyl)acetic acid, and also of the esters of 2-(3,4-dimethoxyphenyl)acetic acid and their reaction in one synthesis step to give hydroxytyrosol.

The following examples serve to further describe the invention.

EXAMPLES a) The compounds of formula (1) are used as such

Example 1

In an apparatus with three-neck flask, stirrer, internal thermometer, metering funnel, reflux condenser and inert gas connection, 25 g (137 mmol) of 2-(3,4-dimethoxyphenyl)ethanol are suspended in 56 g of cumene and heated to reflux temperature, with 481 g of a 21% strength triisobutylaluminum solution in cumene being metered in over the course of 6 hours. The reaction mixture is heated under reflux for a total of 14 h.

After cooling, the reaction mixture is introduced into 256 g of 41.8% strength aqueous citric acid solution. The organic phase is discarded and the aqueous phase is extracted with 150 g of pentane and then several times with ethyl acetate. The pentane phase is discarded and the ethyl acetate phases are combined and washed with 50 g of phosphate buffer pH 7, and the ethyl acetate is removed by distillation.

Yield 19.5 g of hydroxytyrosol, 92% of theory

Example 2

5 g (27.4 mmol) of 3,4-dimethoxyphenylethanol are suspended in 13 ml of cumene, and 79 g of 21% strength (=116 mmol) diisobutylaluminum hydride solution in cumene are metered in with cooling (temp. <30° C.) over 20 min, giving a clear solution. The reaction mixture is heated at 150° C. for 5 h. A sample collection reveals a conversion of 91.8%. After a further 3.5 h at 150° C., the mixture is left to cool and the mixture is added, with ice cooling, to 59 g of 40% strength aqueous citric acid solution. The phases are separated, the organic phase is discarded and the aqueous phase is washed with 30 ml of pentane. The pentane phase is discarded and the aqueous phase is then extracted 4 times with 50 ml of ethyl acetate. The ethyl acetate phases are combined and washed once with 30 g of water. The ethyl acetate is then removed by distillation.

Yield: 3.85 g of 91.1% hydroxytyrosol b) The compounds of formula (1) are produced in situ from compounds of formula (3)

Example 3

In an apparatus with three-necked flask, stirrer, internal thermometer, metering funnel, reflux condenser and inert gas connection, 4.0 g (19 mmol) of methyl 2-(3,4-dimethoxyphenyl)acetate are dissolved in 4 g of xylene, and 13.5 g (95 mmol) of diisobutylaluminum hydride dissolved in 40.5 g of xylene are metered in. When the addition is complete, the reaction mixture is heated to reflux. After reflux for 20 h, the mixture is left to cool and is admixed, with cooling, with 105 g of 20% strength citric acid solution. The xylene phase is discarded and the aqueous phase is extracted once with pentane and three times with 50 ml of ethyl acetate each time. The pentane phase is discarded, the ethyl acetate extracts are combined and the ethyl acetate is removed in vacuo. This gives 2.95 g (88% of theory) of hydroxytyrosol as clear colorless oil.

Example 4

The procedure takes place analogously to example 3 except that the solvent used is diethylbenzene and the reaction temperature is 160° C. After 4 h, the mixture is worked up as described under example 3. Yield: 2.8 g (93%) of hydroxytyrosol as clear colorless oil.

Example 5

2.1 g (10 mmol) of methyl 2-(3,4-dimethoxyphenyl)acetate are dissolved in 30 ml of toluene, and 10 ml of a 1M solution of the lithium aluminum hydride-tetrahydrofuran complex in toluene are added. After reaction for 1.5 h from 38° C. to 50° C., the reaction mixture is admixed with 40 ml of diethylbenzene, and tetrahydrofuran and toluene are distilled off until the boiling temperature of 150° C. is reached. After cooling, 18 g of a 30% strength solution of diisobutylaluminum hydride in diethylbenzene are added and the reaction mixture is then heated at 150° C. for 5.5 h. Work-up takes place as described in example 3. Yield 82%

Comparative Example 1

The procedure takes place analogously to example 3 except that work-up was with 5% strength hydrochloric acid instead of with citric acid solution. The aqueous phase forms an opaque gel, from which no hydroxytyrosol can be isolated.

The invention claimed is:

1. A process for preparing hydroxytyrosol, comprising reacting:
(a) a compound of the general formula (1)

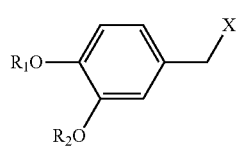

(1)

where X is $CH_2OH$ or $CH_2OM$, wherein M is Li, Na, K, Mg or Ca), $R_1$ and $R_2$ are identical or different and are alkyl radical having 1 to 8 carbon atoms, benzyl radical, alkyl- or halogen-substituted benzyl radical or arylalkyl radical, where $R_1$ and $R_2$ can also be linked via

to give a ring, $R_3$, $R_4$, $R_5$ and $R_6$ are identical or different and are hydrogen or alkyl radical having 1 to 6 carbon atoms, aryl radical, or alkyl-substituted aryl radical, where $R_5$ and $R_6$ can also be linked via $-(CH_2)_4-$, $-(CH_2)_5-$ or $-(CH_2)_6-$ to give a ring, with (b) an aluminum compound of the formula (2)

$$AlR_7R_8R_9 \qquad (2)$$

where $R_7$, $R_8$ and $R_9$ are identical or different and are H or alkyl radical having 1 to 8 carbon atoms, and subsequently adding an aqueous solution of a hydroxycarboxylic acid in an amount such that a clear homogeneous acidic solution with a pH<3 is formed, extracting hydroxytyrosol from the clear homogeneous acidic solution using an organic solvent and removing the organic solvent.

2. The process as claimed in claim 1, wherein the compound of the general formula (1) is a member selected from the group consisting of 2-(3,4-dialkoxy)phenylethanol, 2-(3,4-methylenedioxyphenyl)ethanol, 2-(2,2-dialkylbenzo[1,3]-dioxol-5-yl)ethanol, 2,3-dihydro-1,4-benzodioxin-6-yl)ethanol, and salts thereof.

3. The process as claimed in claim 1, wherein the compound of the general formula (2) is diisobutylaluminum hydride or triisobutylaluminum.

4. The process as claimed in claim 1, wherein the compounds of the formula (1) and the compounds of the formula (2) are used in a molar ratio of compound of formula (1): compound of formula (2) of 1:3 to 1:6.

5. The process as claimed in claim 1, wherein the reaction takes place at a temperature between 0° and 200° C., based on a pressure of 1013 hPa, over a period of 1 to 25 hours.

6. The process as claimed in claim 1, wherein the reaction of the compound of the general formula (1) with the aluminum compound of the general formula (2) takes place in an organic solvent.

7. The process as claimed in claim 6, wherein the solvent is a member selected from the group consisting of toluene, xylene, ethylbenzene, diethylbenzene, 1,3,5-trimethylbenzene, propylbenzene, isopropylbenzene, butylbenzene, cyclic alkylbenzenes and partially hydrogenated naphthalenes.

8. The process as claimed in claim 1, wherein the hydroxycarboxylic acid is a member selected from the group consisting of citric acid, tartaric acid, malic acid and lactic acid.

9. The process as claimed in claim 1, wherein the organic solvent used for the extracting step is a member selected from the group consisting of ethers, carboxylic acid esters, carboxylic acid amides, acetals, ketals, alcohols and alkylamines.

10. The process as claimed in claim 1, wherein the step of removing the organic solvent comprises distillation.

11. The process as claimed in claim 2, wherein the compound of the general formula (2) is diisobutylaluminum hydride or triisobutylaluminum.

12. The process as claimed in claim 11, wherein the compounds of the formula (1) and the compounds of the formula (2) are used in a molar ratio of compound of formula (1): compound of formula (2) of 1:3 to 1:6.

13. The process as claimed in claim 12, wherein the reaction takes place at a temperature between 0° and 200° C., based on a pressure of 1013 hPa, over a period of 1 to 25 hours.

14. The process as claimed in claim 13, wherein the reaction of the compound of the general formula (1) with the aluminum compound of the general formula (2) takes place in an organic solvent.

15. The process as claimed in claim 14, wherein the solvent is a member selected from the group consisting of toluene, xylene, ethylbenzene, diethylbenzene, 1,3,5-trimethylbenzene, propylbenzene, isopropylbenzene, butylbenzene, cyclic alkylbenzenes and partially hydrogenated naphthalenes.

16. The process as claimed in claim 15, wherein the hydroxycarboxylic acid is a member selected from the group consisting of citric acid, tartaric acid, malic acid and lactic acid.

17. The process as claimed in claim 16, wherein the organic solvent used for the extracting step is a member selected from the group consisting of ethers, carboxylic acid esters, carboxylic acid amides, acetals, ketals, alcohols and alkylamines.

18. The process as claimed in claim 17, wherein the step of removing the organic solvent comprises distillation.

* * * * *